US011282243B2

(12) United States Patent
Shin

(10) Patent No.: US 11,282,243 B2
(45) Date of Patent: Mar. 22, 2022

(54) METHOD FOR PROCESSING COMPUTED TOMOGRAPHY IMAGING DATA OF A SUSPECT'S RESPIRATORY SYSTEM

(71) Applicant: Medizinische Hochschule Hannover, Hannover (DE)

(72) Inventor: Hoen-oh Shin, Hannover (DE)

(73) Assignee: MEDIZINISCHE HOCHSCHULE HANNOVER, Hannover (DE)

( * ) Notice: Subject to any disclaimer, the term of this patent is extended or adjusted under 35 U.S.C. 154(b) by 0 days.

(21) Appl. No.: 17/042,712

(22) PCT Filed: Mar. 28, 2019

(86) PCT No.: PCT/EP2019/057874
§ 371 (c)(1),
(2) Date: Sep. 28, 2020

(87) PCT Pub. No.: WO2019/185805
PCT Pub. Date: Oct. 3, 2019

(65) Prior Publication Data

US 2021/0150781 A1 May 20, 2021

(30) Foreign Application Priority Data

Mar. 29, 2018 (EP) .................................... 18164933

(51) Int. Cl.
*G06K 9/00* (2006.01)
*G06T 11/00* (2006.01)
(Continued)

(52) U.S. Cl.
CPC .............. *G06T 11/006* (2013.01); *A61B 6/54* (2013.01); *G06T 7/0016* (2013.01); *G06T 7/38* (2017.01);
(Continued)

(58) Field of Classification Search
CPC ....... G06T 11/006; G06T 7/38; G06T 7/0016; G06T 2207/10081; G06T 2207/30061;
(Continued)

(56) References Cited

U.S. PATENT DOCUMENTS

2004/0101089 A1 5/2004 Karau et al.
2011/0058721 A1 * 3/2011 Zhang .................... A61B 5/091 382/131
(Continued)

OTHER PUBLICATIONS

International Search Report for corresponding PCT Application No. PCT/EP2019/057874 dated Jun. 13, 2019.
(Continued)

*Primary Examiner* — Atiba O Fitzpatrick
(74) *Attorney, Agent, or Firm* — Caesar Rivise, PC

(57) ABSTRACT

A method for processing CT imaging data includes providing CT imaging data obtained at two x-ray energy levels in a first respiratory phase, preferably in an inhalation phase, of the subject and providing second CT imaging data obtained at two x-ray energy levels in a second respiratory phase, preferably in an exhalation phase, of the subject. The method may include reconstructing first regional perfusion blood volume (PBV) imaging data from the provided first CT imaging data, reconstructing second regional PBV imaging data from the provided second CT imaging data, reconstructing first virtual non-contrast (VNC) imaging data from the provided first CT imaging data, reconstructing second VNC imaging data from the provided second CT imaging data, determining a transformation function for registering the first and second reconstructed VNC imaging data, and registering the first and second reconstructed VNC imaging data by applying the transformation function.

19 Claims, 4 Drawing Sheets providing first CT imaging data obtained at least at two x-ray energy levels in a first respiratory phase of the subject ~ S1
providing second CT imaging data obtained at least at two x-ray energy levels in a second respiratory phase of the subject ~ S2
reconstructing first regional PBV imaging data from the provided first CT imaging data ~ S3
reconstructing second regional PBV imaging data from the provided second CT imaging data ~ S4
reconstructing first VNC imaging data from the provided first CT imaging data ~ S5
reconstructing second VNC imaging data from the provided second CT imaging data ~ S6
determining a transformation function T for registering the first and second VNC imaging data ~ S7
registering the first and second VNC imaging data by applying said transformation function T ~ S8
calculating regional ventilation data using the registered first and second VNC imaging data and/or T ~ S9
registering the first and second PBV imaging data by applying said transformation function T ~ S10
adjusting the first reconstructed regional PBV imaging data for different blood volume fractions caused by the different respiratory phases ~ S11

(51) Int. Cl.
*G06T 7/38* (2017.01)
*A61B 6/00* (2006.01)
*G06T 7/00* (2017.01)

(52) U.S. Cl.
CPC ............... *G06T 2207/10081* (2013.01); *G06T 2207/30061* (2013.01); *G06T 2207/30104* (2013.01); *G06T 2211/408* (2013.01)

(58) Field of Classification Search
CPC ..... G06T 2207/30104; G06T 2211/408; A61B 6/54
See application file for complete search history.

(56) References Cited

U.S. PATENT DOCUMENTS

2011/0286652 A1 11/2011 Kabus et al.
2013/0303899 A1* 11/2013 Mistry ................. A61B 6/5217 600/425

OTHER PUBLICATIONS

Castillo et al., “Ventilation From Four-Dimensional Computed Tomography: Density Versus Jacobian Methods”, Physics in Medicine and Biology, vol. 55, No. 16, pp. 4661-4682 (2010).
Chae et al., Xenon Ventilation CT With a Dual-Energy Technique of Dual-Source CT: Initial Experience1, Radiology, vol. 248, No. 2, pp. 615-624, Aug. 2008.
Ding et al., “Comparison of Image Registration Based Measures of Regional Lung Ventilation From Dynamic Spiral CT With Xe-CT”, Medical Physics, vol. 39, No. 8, pp. 5084-5098, Aug. 2012.
Grant et al., “Assessment of an Advanced Image-Based Technique to Calculate Virtual Monoenergetic Computer Tomographic Images From a Dual-Energy Examination to Improve Contract-to-Noise Ratio in Examinations Using Iodinated Contract Media”, Investigative Radiology, vol. 49, No. 9, pp. 586-592, Sep. 2014.
Guerrero et al., “Dynamic Ventilation Imaging From Four-Dimensional Computed Tomography”, Institute of Physics Publishing, vol. 51, No. 4, pp. 777-791, Feb. 2006.
Hachulla et al., “Dual-Energy Computed Tomographic Imaging of Pulmonary Hypertension”, Swiss Medical Weekly, 2016;146:w14328.
Hwang et al., “The Role of Dual-Energy Computed Tomography in the Assessment of Pulmonary Function”, European Journal of Radiology, vol. 86, pp. 321-334, Jan. 2017.
Kaza et al., “Dual-Energy CT With Single- and Dual-Source Scanners: Current Applications in Evaluating the Genitourinary Tract”, RadioGraphics, vol. 32, No. 2, pp. 353-369, Mar.-Apr. 2012.
Oliveira et al., “Medical Image Registration: A Review”, Computer Methods in Biomechanics and Biomedical Engineering, pp. 1-21, 2012.
Schabel et al., “Assessment of the Hepatic Veins in Poor Contract Conditions Using Dual Energy CT: Evaluation of a Novel Monoenergetic Extrapolation Software Algorithm”, RöFo, 186, 591 (2014).
Thieme et al., “Pulmonary Ventilation and Perfusion Imaging With Dual-Energy CT”, European Radiology, vol. 20, Issue 12, pp. 2882-2889, Dec. 2010.
Zhang et al., “Dual-Energy CT Lung Ventilation/Perfusion Imaging for Diagnosing Pulmonary Embolism”, European Radiology, vol. 23, Issue 10, pp. 2666-2675, Oct. 2013.
McCollough et al., “Dual-Energy Algorithms and Postprocessing Techniques” in Dual Energy CT in Clinical Practice, Medical Radiology, Springer (2011), Abstract and Introduction.

* cited by examiner

METHOD FOR PROCESSING COMPUTED TOMOGRAPHY IMAGING DATA OF A SUSPECT'S RESPIRATORY SYSTEM

CROSS-REFERENCE TO RELATED APPLICATIONS

This application is a U.S. National Phase Application under 35 U.S.C. § 371 of PCT/EP2019/057874, filed Mar. 28, 2019, which claims priority from EP 18164933.6, filed Mar. 29, 2018, the contents of which applications are incorporated herein by reference in their entireties.

BACKGROUND OF THE INVENTION

The invention relates to a method for processing computed tomography (CT) imaging data. In particular, the invention relates to method which enables a combined assessment of anatomical, ventilation and perfusion information of a subject's respiratory system with high resolution. Furthermore, the method enables to compare all these information at the regional level. In addition, the invention relates to a CT scanning unit, comprising a control device which is able to perform the claimed method. Applications of the invention are available in medical CT imaging, in particular in quantitative dual-energy CT lung imaging.

The main function of an organism's respiratory system is gas exchange of oxygen and carbon dioxide between inhaled air and circulating blood at the lung periphery. For this purpose adequate ventilation, perfusion, and matching of ventilation and perfusion are necessary. Disease or injury conditions can affect the ventilation and/or perfusion status of an organism or alter the relationship between ventilation and perfusion. Therefore, in addition to the evaluation of morphological changes in the respiratory system, also the assessment of the pulmonary function is important to identify various pulmonary diseases.

Several techniques are known in the prior art to measure the pulmonary function, such as planar scintigraphy (PS), single-photon emission computed tomography (SPECT) and positron emission tomography (PET). However, all of these methods only have a low spatial resolution and present challenges regarding the generation of the radioactive tag. Furthermore, in order to address the morphology of the respiratory system also, all methods demand for additional measurements using a technique with high spatial resolution such as computed tomography (CT). This separate evaluation of pulmonary function (ventilation/perfusion) and anatomic changes with various modalities prevents a direct comparison of the different regional information and increases the radiation burden for the subject. As a consequence, these limitations triggered the simultaneous evaluation of functional and anatomical changes with only one modality.

For the anatomic evaluation of the lung, computed tomography (CT) has become the modality of choice, since it produces excellent anatomic images and is broadly available. But standard CT imaging does typically not provide for a functional assessment. However, by using the radiographic contrast enhancement property of non-radioactive xenon gas, CT is able to measure the pulmonary ventilation, i.e. the rate at which new air reaches the gas exchange area of the lungs. Therefore, inert xenon (Xe) is inhaled and exhaled during imaging and the regional ventilation is calculated by observing the wash-in and wash-out rates on serial CT images. Xe, as well as the associated hardware to control the gas are expensive, and its application is complex and time consuming. Xenon gas is also known to have a strong anesthetic effect. The use of Xe-enhanced CT measurements in human subjects are therefore rather limited.

Besides the evaluation of pulmonary ventilation, CT imaging can also assess the lung perfusion blood volume (PBV). This metric reflects the regional volume of blood to which fresh blood is being delivered. To measure the PBV a CT-contrast enhancing agent, such as iodine, is distributed in the blood vessels of the respiratory system under investigation. If this fresh delivery of blood is equilibrated with an amount of iodine, then the measured regional iodine concentration reflects the regional PBV which serves as a surrogate for the pulmonary parenchymal perfusion. When using conventional (single energy) CT the respective iodine concentration maps can be created by subtracting a pre-contrast-scan from a contrast-enhanced (post-contrast) scan, preferably under identical conditions (e.g. same respiratory phase).

As outlined above, computed tomography is, therefore, generally capable of providing regional anatomic as well as regional functional information (ventilation/perfusion) with a high spatial resolution. However, since each of the functional measurements requires a corresponding reference measurement, i.e. for the ventilation an inspiration/expiration measurement and for the perfusion a pre- and post-contrast-scan, recording morphological, ventilation, and perfusion information is in total a time-consuming task, associated with a relatively high radiation dose for the subject. Furthermore, a direct regional comparison of the different functional and morphological data is difficult, due to misregistration of the different images caused by movements of the subject between the single scans.

These problems of long measuring times and misregistrations can be overcome to some extend by using a recently developed technique called dual-energy computed tomography (DECT). An overview over the different setups and technical aspects can be found, for example, in the review-article of Kaza et al. [1]. The method utilises two separate, quasisimultaneously recorded CT-datasets of the same anatomic location taken at different energies (e.g. at 80 kVp and 140 kVp) to differentiate between the contrast agent (e.g. iodine) and normally present materials such as air, blood, and soft tissue within a "single" scan. This differentiation is based on the characteristic energy-dependent attenuation properties of the different materials. For example, the attenuation of iodine increases more markedly than that of calcium (bones) with decreasing x-ray photon energy. Since data and corresponding reference data are quasi-simultaneously measured, changes in contrast enhancement (xenon or iodine) and/or spatial misregistration problems can almost be excluded, which clearly improves the quality of the obtained functional data over traditional single energy CT. Furthermore, the time and the costs to acquire such functional data is reduced, while keeping the radiation dose level similar to those with conventional CT.

Though the DECT technique can improve functional data acquisition, as outlined above, the collection of lung ventilation data as well as the combined assessment of ventilation and perfusion data via DECT is up to now hardly used for diagnostics. This is because the known scan protocols for DECT ventilation scanning (e.g., Chae et al. [2]., Thieme et al. [3], and Zhang et al. [4]) are merely based on xenon-enhanced measurements, including all the mentioned drawbacks like high costs, strong anesthetic effect, etc. As a consequence the collection of Xe-based ventilation data is not approved for clinical use in many countries which limits the fast and reliable combined assessment of perfusion, ventilation and morphological information of the respiratory system.

SUMMARY

Accordingly, an advantage of the invention is to provide an improved method to gain this in formation of a subject's respiratory system which avoids the disadvantages of conventional techniques, especially the need for Xe-enhanced imaging data. In particular, an advantage of the invention is to provide a method of CT imaging data processing which provides combined quantitative anatomic, perfusion, and ventilation information of the lung which can be directly compared on the regional level, thereby, increasing sensitivity, spatial resolution, and reproducibility. A further advantage is to provide a method for processing CT imaging data with which the required raw imaging data can be acquired with a low radiation burden for the subject and low time spans.

These advantages are solved by the independent claims. Preferred embodiments and applications of the invention are defined in the dependent claims.

According to a general aspect of the invention, the above advantages are solved by a method of processing CT imaging data, preferably dual-energy or multi-energy CT imaging data, of a subject's respiratory system. Thereby, the subject has a CT-contrast enhancing agent, e.g. iodine, distributed in its blood vessels. The method comprises the steps of providing CT imaging data obtained at least at two x-ray energy levels in a first respiratory phase, preferably in an inhalation phase, of the subject and providing second CT imaging data obtained at least at two x-ray energy levels in a second respiratory phase, preferably in an exhalation phase, of the subject. The method further comprises reconstructing first regional PBV imaging data from the provided first CT imaging data, reconstructing second regional PBV imaging data from the provided second CT imaging data, reconstructing first virtual non-contrast (VNC) imaging data from the provided first CT imaging data, and reconstructing second VNC imaging data from the provided second CT imaging data. The method further comprises determining a transformation function T for registering the first and second reconstructed VNC imaging data and registering the first and second reconstructed VNC imaging data by applying said transformation function T. Further the method comprises calculating regional ventilation imaging data using the registered first and second reconstructed VNC imaging data and/or the determined transformation function T.

Advantageously, the image processing method provides four registered imaging data sets (one ventilation data set, one PBV data set from one respiratory phase, and two VNC data sets from two respiratory phases), including three types of information, which can be regionally compared voxel by voxel. This enables a more precise evaluation of or correlation between the morphological and functional information of the respiratory system which does not require any use of Xe-gas as a contrast agent. Furthermore, the method enables a combined assessment of morphological and functional (perfusion and ventilation) information from only two CT scans in different respiratory phases, i.e. possibly during one breath. Thus, by combining the dual- or multi-energy technique with the determination of pulmonary ventilation via analysing the lung deformation, measuring time, radiation burden as well as mental and physical stress for the subject can be reduced.

In this context the term "processing" of CT imaging data should be understood as a manipulation of items of CT imaging data to produce meaningful information, whereby CT imaging data, as used herein, refers to any data type of the group of two dimensional (2D) CT images, three dimensional (3D) CT images and volumetric CT data from which various 2D and 3D CT images can be formed. Preferably, the volumetric CT data comprises a plurality of voxels (volume elements), each voxel assigned to a location in three-dimensional space by three spatial coordinates x, y, z of a Cartesian coordinate system and a volume data value, e.g. an 8-bit or 12-bit value.

"Providing" such CT imaging data might comprise supplying respective (raw) CT imaging data directly after acquisition but also providing (raw) CT imaging data, measured and stored beforehand, via a data storage medium, e.g. a magnetic or optical disc, or via a data communication network. In other words the process of collecting the (raw) CT imaging data and the subsequent processing of the CT imaging data can be separated in time and space. The provided CT imaging data can comprise dual-energy CT, multi-energy CT and/or conventional CT imaging data, as long said first and second provided CT imaging data include imaging information of at least two different x-ray energy levels respectively, e.g. two data sets of the same anatomic location taken at beam energies of 80 kVp and 120 kVp. However, preferably the at least two x-ray energy levels of each first and second CT imaging data are corecorded or obtained quasi-simultaneously, i.e. with a time delay below 1 second. In addition, the provided CT imaging data can also comprise photon-counting CT data, i.e. dual-energy, multi-energy and/or conventional CT imaging data recorded by a photon-counting detector which registers the interactions of individual photons. Due to the high spectral resolution of this technique this allows, for example, a better separation of the VNC and the PBV imaging data.

Furthermore, the provided first and second CT imaging data might be obtained in a particular respiratory phase, e.g. inspiration, end-inspiration, expiration, or end-expiration. Thereby, inspiration or inhalation refers to a process of air entering the lung, while expiration or exhalation refers to a process where the air is released from the lungs. In this context the term respiratory phase can also be understood as a certain stage in the respiratory cycle, a certain amount of air present in the lung, or a certain level of lung inflation. Preferably the first and second CT imaging data are obtained in different respiratory phases. Therefore, the subject can, for example, inhale and then hold his breath for several seconds. During this time the first CT imaging data might be recorded. Subsequently the subject can exhale and then again hold his breath for several seconds. During that time the second CT imaging data can be recorded.

For reconstructing the first and second regional PBV as well as the VNC imaging data the provided data sets obtained at least at two x-ray energy levels in each respiratory phase are used. Based on the x-ray energy-dependent change in attenuation of the different materials present in the subject—usually air, soft tissue and blood (via the contrast agent)—the first and second CT imaging data can be decomposed in material-density data which reflect the regional distribution of the different materials, allowing also for a subtraction of one material type from the other. Voxels that show an energy-dependent change in attenuation resembling the attenuation of the contrast agent might then be represented in the PBV imaging data, while on the other hand VNC imaging data can be generated by removing the attenuation resembling the attenuation of the contrast agent from the original imaging data. Consequently, the PBV imaging data can also be described as a distribution map of the contrast agent, while the VNC imaging data provide information equivalent to that obtainable from unenhanced images obtained before the administration of the contrast agent. For reconstructing the different imaging data several algorithms and techniques are presently known which are described in detail in reference [5]. All of these are in principle suitable for reconstructing the first and second PBV and VNC imaging data of the claimed imaging processing method.

In the subsequent step of determining the transformation function T a spatial transformation T may be determined that matches the first and second reconstructed VNC imaging data, preferably by minimizing or maximizing a similarity measure also known as cost function. Such cost functions can include a term related to the voxel intensity or structures similarity and a term related to the deformation field. An overview of state of the art methods for the determination of transformation functions T, as well as usual definitions of cost functions can be found in the review of F. P. M. Oliveira and J. M. R. S. Tavares [6] and the citations therein. In the case of the claimed method the determination of T can be based on the VNC imaging data itself, i.e. the first and second VNC imaging data is used as reference and floating/target data, but it is also possible to determine T based on PBV, morphological or any other type of imaging data reconstructed from the original first and second (raw) CT imaging data.

Once the transformation function T is determined, in the next step of the claimed method the first and second reconstructed VNC imaging data are registered by applying said transformation function T. Depending on the choice of reference and floating/target data, either the first reconstructed VNC imaging data may be registered or matched on the second reconstructed VNC imaging data, or vice versa. However, in the end two registered VNC imaging data sets are available which can be regionally compared voxel by voxel, though the original (raw) data was measured preferably in different respiratory phases.

Finally, regional ventilation imaging data can be calculated based on this registered first and second reconstructed VNC imaging data or the determined transformation function T. The ventilation data shows the regional change in air content within the lungs. In order to assess this local air volume change between the first and second respiratory phase, different measures are known, either based on the registered VNC imaging data and/or the determined transformation function T. On the one hand the regional volume change can be derived via comparing the fractional air content in corresponding voxels of the first and second registered VNC imaging data. Thereby, the air content is given by the respective image CT value of the voxel. Alternatively, methods based on the transformation function T can be used. For this purpose the Jacobian of T, i.e. the total derivative of the deformation field, is calculated. Thereby, the Jacobian measures the differential expansion or contraction at a position in the imaging data from which the regional ventilation can be deduced. Since this ventilation measure depends only on the transformation function T, advantageously, uncertainties resulting from image noise, acquisition artefacts and reconstruction artefacts can be avoided. Details on the different approaches as well as further corrections can be found in the references [7-9], as well in the citations therein.

According to another aspect of the invention, the method may further comprise the step of registering the first and second reconstructed regional perfusion blood volume imaging data by applying said transformation function T. Using the same transformation function T for registering is possible since the first and second reconstructed regional PBV imaging data were reconstructed from the same CT imaging data sets as the first and second reconstructed VNC imaging data. Therefore, once said transformation function T is determined, it can be used to register the first and second reconstructed VNC imaging data, as well as the first and second reconstructed regional PBV imaging data respectively.

Advantageously, this allows for a fast registration of the first and second reconstructed regional PBV imaging data while reducing the required computational effort. As a result, another registered imaging data set is added to the previous ones, resulting in total in five registered imaging data sets (one ventilation data set, two PBV data sets from two respiratory phases, and two VNC data sets from two respiratory phases) which can be regionally compared voxel by voxel. Advantageously, this results in a better comparability of the first and second PBV imaging data and facilitates any subsequent diagnostic procedure.

However, since the dual-energy computed tomography imaging data sets were preferably obtained in two different respiratory phases, i.e. at two different points in time, the reconstructed regional PBV imaging data might contain different blood volume fractions in the lung in the different respiratory phases. For example, in expiration the fraction of air may decrease while the fraction blood may increase. In order to correct for such effects, another aspect of the invention may comprise the step of adjusting the first and/or second reconstructed regional PBV imaging data for different blood volume fractions caused by the different respiratory phases.

By way of example, for this correction the regional change of blood volume may be calculated based on the registered VNC imaging data analogously to the computation of the regional air volume change for the ventilation data, as outlined in reference [9]. In detail the first and second registered VNC imaging data may be compared voxel by voxel in order to derive a regional change of the fractional blood content or an overall change of density in corresponding voxels. Thereby, the blood content is given by the respective image CT value of the voxel. Based on this regional change of the blood volume the first and/or second reconstructed regional PBV imaging data is then scaled regionally in order to compensate for the different blood volume fractions. Alternatively, the adjustment might also be based on the determined transformation function. Advantageously, this adjustment improves the comparability of the first and second PBV imaging data further and facilitates any subsequent functional analysis.

Although the present registered first and second reconstructed VNC imaging data provide adequate anatomical information, it is also possible to calculate additional morphological imaging data, contrast optimized for diagnostic purpose. Therefore, according to another aspect of the invention, the method may further comprise the step/steps of reconstructing first morphological imaging data from the provided first CT imaging data of the first respiratory phase; and/or reconstructing second morphological imaging data from the provided second CT imaging data of the second respiratory phase. In this context, the first and second morphological imaging data comprise reconstructed CT images that are equivalent to images that shows attenuation as if a single monochromatic energy (kVp) were used to scan. Hence, instead of morphological imaging data also the expression mono-energetic imaging data can be used. The claimed post-processing may be achieved in image space by the extrapolation of the (raw) CT imaging data obtained at least at two x-ray energy levels, e.g. at 80 kVp and 120 kVp, into single kVp, e.g. ranging from 40 to 160 kVp. For this purpose known monochromatic reconstruction algorithms can be used such as presented in [10] and [11] and the references therein. By adjusting the energy level of the image output the contrast between different materials can be optimized, as well as hardening and metal artefacts reduced. Furthermore, the first and second morphological imaging data can additionally be registered by applying again said transformation function T.

According to another aspect, the first CT imaging data obtained at least at two x-ray energy levels in a first respiratory phase and/or the second CT imaging data obtained at least at two x-ray energy levels in a second respiratory phase may be provided by acquiring the CT imaging data using a CT scanner, preferably a multi-energy or dual-energy CT scanner. In other words, according to this aspect the method also includes the process of actively generating the raw CT imaging data which is used for the subsequent steps of processing the obtained imaging data. For this purpose for example a dual-source dual-energy CT scanner, a single-source dual-energy CT scanner with fast kilovoltage switching, a single-source dual-energy CT scanner with dual detector layers, or multi-energy CT scanner may be used. Advantageously, this aspect enables a direct control over the scanned region and the quality of the acquired data.

According to yet another aspect, in the step of determining the transformation function T the first and second reconstructed VNC imaging data may be used as reference data and floating data to determine the transformation function T which maps an image point in the reference data to the corresponding image point in the floating data. This includes that the first reconstructed VNC imaging data is used as reference data and the second reconstructed VNC imaging data is used as floating data, as well as that the second reconstructed VNC imaging data is used as reference data and the first reconstructed VNC imaging data is used as floating data. Depending on the choice, the transformation function T maps the first reconstructed VNC imaging data to the second reconstructed VNC imaging data, or vice versa.

Because the reconstructed VNC imaging data sets usually include salient and distinctive objects, such as bronchi or blood vessels, which can be used as reliable markers for determining the transformation function T, according to this aspect the reliability and accuracy of T and thus the reliability and accuracy of the imaging processing method as a whole is improved. Furthermore, by using the reconstructed VNC imaging data sets to determine the transformation function T, also the first and second reconstructed morphological imaging data can be used as reference and floating data. Both the reconstructed VNC imaging data and also the reconstructed morphological imaging data sets usually provide prominent features which facilitate the determination of T which is e.g. based on the mutual spatial assignment of this markers in the different data sets.

According to another aspect of the invention, the second CT imaging data of the second respiratory phase may be obtained in a different respiratory phase, but in the same respiratory cycle with respect to the first respiratory phase. In other words the dual-energy CT imaging data may be obtained during one breath. For example, the first CT imaging data may be acquired during a breath hold in maximum inspiration, then the subjects exhales, and subsequently the second CT imaging data is acquired during a breath hold in maximum expiration. By this the time between the acquisition of the two CT imaging data sets is minimized which, advantageously, saves time, increases their comparability, and also reduces the risk of imaging artefacts due to movements of the subject.

Alternatively, the dual-energy computed tomography imaging data of the second CT imaging data of the second respiratory phase may be obtained in a different respiratory phase and a different respiratory cycle; and/or between 2 and 15 minutes, particularly preferred 5 minutes, after the first respiratory phase. Though this procedure might increase the risk of risk of imaging artefacts due to movements of the subject, it can provide additional information due to a change in the enrichment of the CT-contrast enhancing agent in the different organs and tissues with time. Advantageously, such known dynamic effects in contrast enhancement after the administration of the contrast agent, e.g. delayed enhancement or late enhancement, can facilitate a later detection of various pulmonary diseases based on the imaging data (especially in the reconstructed PBV and morphological imaging data) provided by the claimed method.

According to a further aspect of the invention, the first and second CT imaging data may be obtained each at exactly two x-ray energy levels by using a dual-energy CT scanner or a multi-energy CT scanner. In other words, the first CT imaging data is obtained at exactly two x-ray energy levels, e.g. 80 kVp and 120 kVp, and also the second CT imaging data is obtained at exactly two x-ray energy levels, e.g. 80 kVp and 140 kVp. Thereby, the two x-ray energy levels at which the respective CT imaging data sets were obtained can be different, identical, or partly identical, as in the example above. For this purpose, different types of dual-energy CT scanners might be used such as dual-source dual-energy CT scanner, single-source dual-energy CT scanner with fast kilovoltage switching, or single-source dual-energy CT scanner with dual detector layers. Furthermore, also a multi energy CT scanner may be used which is configured to provide data sets of two energy levels only. Advantageously, this aspect of the invention enables a fast reconstruction of the first and second regional PBV as well as the VNC imaging data, because data of only two energy levels has to be considered in each reconstruction step.

Alternatively, the first and second CT imaging data are obtained each at more than two x-ray energy levels each by using a multi-energy CT scanner. For example, the first CT imaging data includes spectra obtained at 40 kVp, 80 kVp, 120 kVp, and 140 kVp, while the second CT imaging data includes spectra obtained at 40 kVp, 60 kVp, and 80 kVp. In this context, the number of obtained energy levels of the first and second CT imaging data, as well as their respective energy level values might be identical or different. By including more than two energy spectra for reconstructing the PBV and VNC imaging data, advantageously, the reliability and accuracy of these steps increases.

According to a further aspect of the invention, two x-ray energy levels of the first CT imaging data and two x-ray energy levels of the second CT imaging data may be identical, partly identical, or different. While identical or partly identical energy levels might enable a fast data acquisition, since no or only minor changes in the scanner setup have to be made, the use of different x-ray energy levels might provide additional visual information for later diagnostics. Due to the energy-dependent attenuation properties of the different materials the use of different x-ray energy levels can provide additional contrast in the acquired CT imaging data.

According to another aspect of the invention, the method may further comprise the steps of providing third CT imaging data obtained at least at two x-ray energy levels in a third respiratory phase of the subject. Further, the method comprises reconstructing third regional PBV imaging data from the provided third CT imaging data of the third respiratory phase and reconstructing third VNC imaging data from the provided third CT imaging data of the third respiratory phase. The method comprises further determining a second transformation function $T_2$ for registering the third VNC imaging data with the first or second reconstructed VNC imaging data and registering the third and first or second reconstructed VNC imaging data by applying said second transformation function $T_2$. Further, the method comprises calculating second regional ventilation imaging data using the registered third and first or second reconstructed VNC imaging data and/or the determined second transformation function $T_2$. In other words, the claimed method for processing CT imaging data can be extended to include CT imaging data of further respiratory phases of the subject. Though this aspect is described in detail with respect to the use of CT imaging data of three respiratory phases, the method is particularly not limited to three and persons skilled in the art will appreciate that it can be easily extended to include data of further respiratory phases. For all steps (reconstructing, determining, registering, and calculating) the same procedures or algorithms can be used as in the corresponding steps described before, with the difference that they are applied to different (raw) imaging data. By including data of further respiratory phases this aspect advantageously provides additional morphological as well as functional information and increases the reliability and accuracy of the method at the same time.

According to another aspect of the invention, the spatial resolution of the first and second reconstructed regional PBV imaging data and the calculated regional ventilation imaging data may be below 5 mm, preferably below 2 mm. This enables quantitative regional functional pulmonary information with high sensitivity.

A further general subjects of the invention is a computer program product, comprising a sequence of machine instructions which causes a computer performing an method according to any one of the above mentioned aspects, when executing the sequence of machine instructions.

Another general subject of the invention is a medium on which an embodiment of the just mentioned computer program product is stored. The medium (e.g., non-transitory storage medium) may be magnetic (e.g., a floppy disk or a hard drive) or optical (e.g., a compact disk read only memory, or "CD ROM"), and may be read only or random access. If the computer program product is transmitted from a website, server, or other remote source using a physical cable, digital subscriber line (DSL), or wireless technologies then the physical cable, DSL, or wireless technologies such as infrared, radio, and microwave are included in the definition of medium.

A further general subject of the invention a computer on which an embodiment of the above mentioned computer program product is stored and which is processable by the computer. Therefore, the computer may be configured to perform arithmetical, logical, and input/output operations, according to the machine instructions encoded in the computer program product. The computer may be configured to only process the imaging data acquired by any CT data acquisition device somewhere else, or, according to another aspect, the computer is formed as a control device for a CT scanning unit, i.e. the computer is directly coupled to a CT scanning unit.

Another general subject of the invention is a multi-energy or dual-energy CT scanning unit comprising a control device or a computer which is formed as a control device, both configured to perform a method according to any of the above mentioned aspects.

Further details and advantages of the invention are described in the following with reference to the attached drawings, which show in:

DETAILED DESCRIPTION

Figure 1:
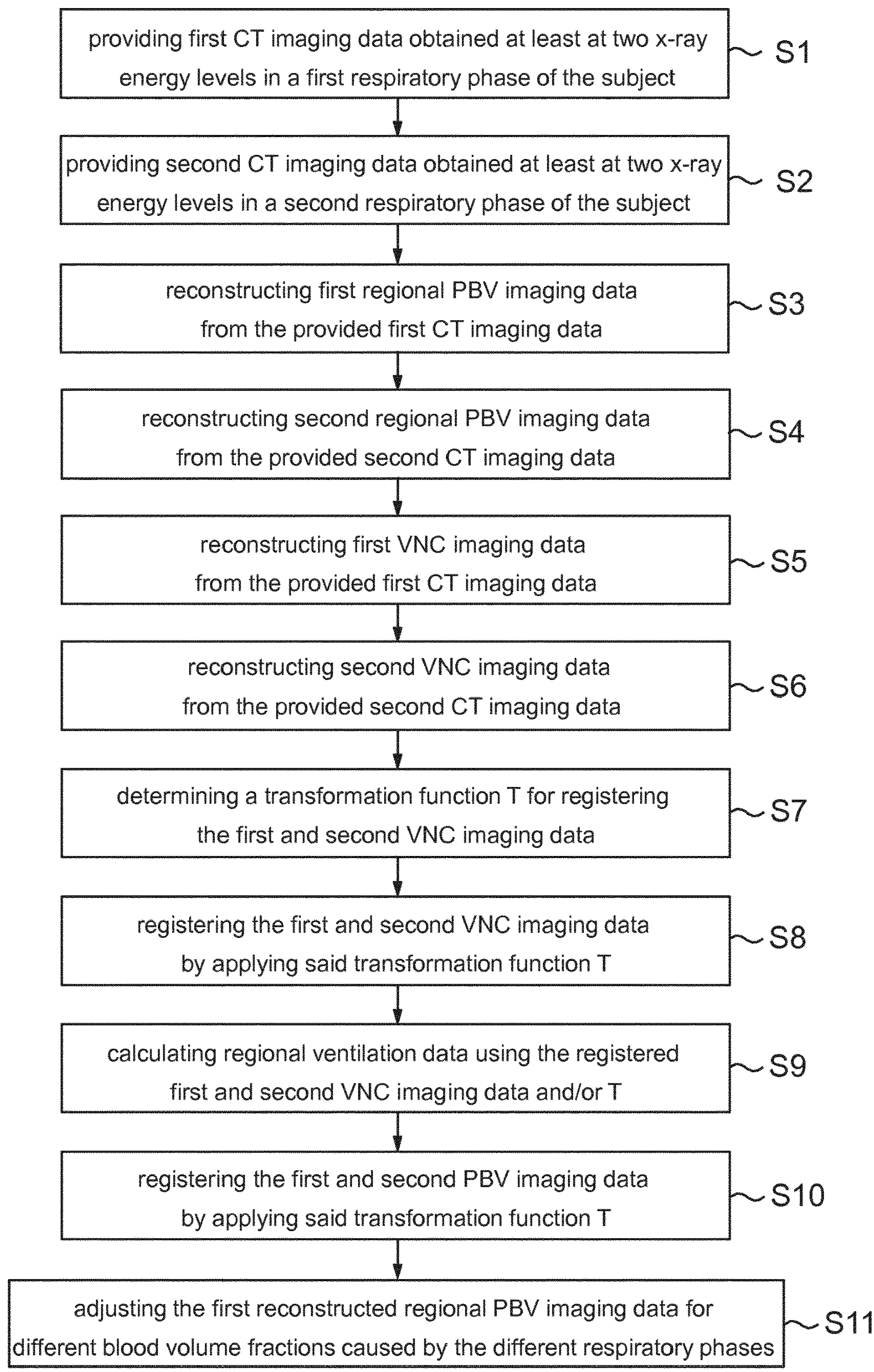
FIG. 1: A flowchart illustrating a method for processing CT imaging data according to an embodiment of the invention.

According to FIG. 1, the method of the invention comprises the steps of providing first (S1) and second (S2) imaging data, reconstructing first (S3) and second (S4) regional PBV imaging data, reconstructing first (S5) and second (S6) VNC imaging data, determining a transformation function T (S7), registering the first and second reconstructed VNC imaging data (S8), calculating regional ventilation imaging data (S9), registering the first and second reconstructed PBV imaging data (S10), and adjusting the first reconstructed regional PBV imaging data for blood volume variations (S11).

It should be noted that although the flowcharts describe the operations as sequential processes, many of the operations may be performed in parallel, concurrently or simultaneously. In addition, the order of some operations may be re-arranged. The processes may be terminated when their operations are completed, but may also have additional steps not included in the figure. The processes may correspond to methods, functions, procedures, subroutines, subprograms, etc.

In the following the individual steps of FIG. 1 are described with further details.

In steps S1 and S2 first and second CT imaging data, e.g. series of 2D CT images which might be measured and stored beforehand, are provided, whereby each of said first and second CT imaging data was obtained at least at two x-ray energy levels and in a certain respiratory phase of the subject. Furthermore, the subject had a CT-contrast enhancing agent distributed in its blood vessels, preferably in the pulmonary blood pool, while said CT imaging data was obtained. This can be achieved by administering an contrast agent, e.g. iodine, containing infusion. Preferably both CT imaging data were obtained by using a dual-source dual-energy CT scanner, enabling a quasi-simultaneously acquisition of a high and low photon energy spectrum of the same anatomic location within a single CT scan. Particularly preferred said first and second CT imaging data were obtained in different respiratory phases, e.g. first CT imaging data was obtained in an inhalation phase, while the second CT imaging data was obtained in an exhalation phase.

In steps S3 and S4 first and second regional pulmonary perfusion blood volume imaging data are reconstructed from the respective first and second CT imaging data. For this purpose the first and second CT imaging data, each including spectra of at least two x-ray energy levels, are respectively analysed for specific x-ray energy-dependent changes in attenuation caused by the presence of the contrast agent. The resulting distribution map of the contrast agent in the first and second CT imaging data is then represented in the respective PBV imaging data, reflecting the regional distribution of the contrast agent in the pulmonary system.

In steps S5 and S6 first and second virtual non-contrast imaging data are reconstructed from the respective first and second CT imaging data. These first and second VNC imaging data might provide information equivalent to that obtainable from unenhanced images measured before the administration of the contrast agent. For this purpose the attenuation of the contrast agent is removed from the original imaging data.

In step S7 a transformation function T for registering the first and second VNC imaging data is determined. Thereby, T might include a combination of basic transformations such as rotations, translations, scalings, and/or shearings, in order to align the first and second reconstructed VNC imaging data. For determining said transformation function T, for example, a feature-based registration can be used, including the steps of detecting feature points in both data sets, finding corresponding pairs of feature points and constructing a transformation function T which minimizes a measure of mismatch between corresponding pairs of feature points in both data sets. However, also other methods as described in reference [8] can be used.

In step S8 the first and second VNC imaging data are registered by applying the determined transformation function T. Depending how the transformation function T was determined, either the first reconstructed VNC imaging data might be registered on the second reconstructed VNC imaging data, or vice versa. However, in the end two registered VNC imaging data sets are available which can be regionally compared voxel by voxel.

In step S9 regional ventilation data is calculated using the registered first and second VNC data and/or said transformation function T. In order to calculate this ventilation data which shows the change in air content due to ventilation, for example, fractional air content in corresponding voxels of the first and second registered VNC imaging data can be compared. Alternatively, the Jacobian of the transformation function T which measures the differential expansion or contraction at a position in the imaging data might be used.

In step S10 the first and second PBV imaging data are registered by applying said determined transformation function T. Using here the same transformation function T for registering as in the case of the VNC imaging data is possible since the first and second reconstructed regional PBV imaging data were reconstructed from the same CT imaging data sets as the first and second reconstructed VNC imaging data. Therefore, once said transformation function T is determined, it can be used to register the first and second reconstructed VNC imaging data, as well as the first and second reconstructed regional PBV imaging data respectively.

In step S11 the first reconstructed and registered regional PBV imaging data is adjusted for different blood volume fractions caused by the different respiratory phases. For this correction in a first step the regional change of the blood volume fraction between corresponding voxels of the first and second registered VNC imaging data is determined by comparing the image CT values of the respective voxels. Based on this regional change of the blood volume the first reconstructed regional PBV imaging data is then scaled accordingly to compensate for this change.

In the end, the method presented in FIG. 1 results in five registered imaging data sets (1 ventilation, 2 PBV from two respiratory phases, and 2 VNC from two respiratory phases), including three types of information, which can be regionally compared voxel by voxel. By this a more precise evaluation of or correlation between the morphological and functional information of the respiratory system is possible.

Figure 2:
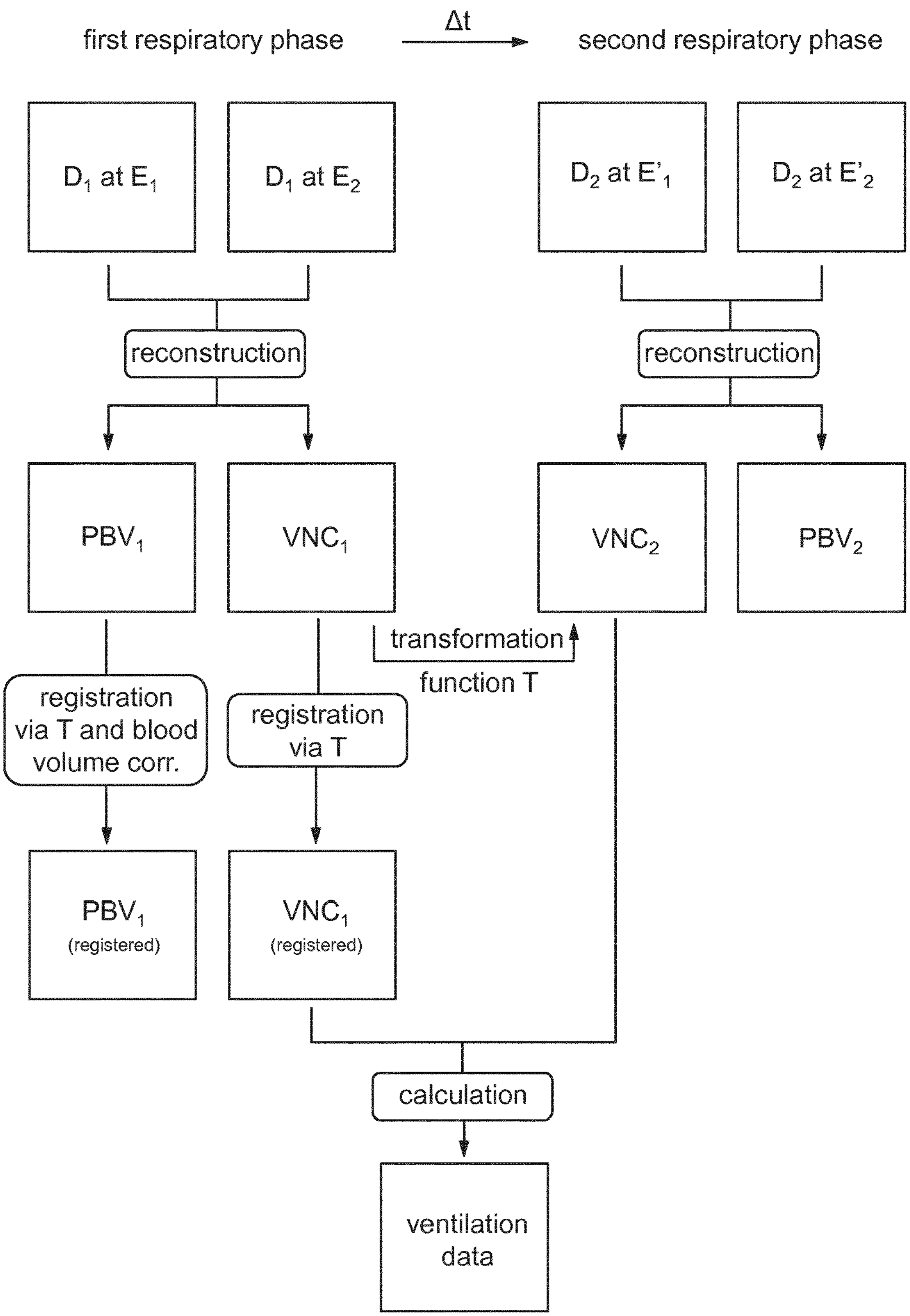
FIG. 2: Schematic illustration (processing pipeline) of an embodiment of the CT image processing method.

FIG. 2 schematically illustrates an embodiment of the image processing method. For a better understanding the operations are illustrated in an more figurative manner (processing pipeline), rather than showing a sequential process. Initially first and second (raw) CT imaging data $D_1$ and $D_2$ are provided. Thereby, $D_1$ was obtained in a first respiratory phase of the subject, e.g. in end-inspiration, and includes two, preferably co-recorded, data sets of the same anatomic location obtained with x-ray energy levels $E_1$ and $E_2$. Accordingly, $D_2$ was obtained in a subsequent second respiratory phase of the subject, e.g. in end-expiration, and includes two, preferably co-recorded, data sets of again the same anatomic location obtained with x-ray energy levels $E'_1$ and $E'_2$. In order to facilitate the data evaluation $E'_1$ and $E_1$, as well as $E'_2$ and $E_2$ might have the same value, e.g. $E'_1=E_1=80$ kVp and $E'_2=E_2=120$ kVp. From each of the first and second CT imaging data first and second PBV as well as VNC imaging data are reconstructed respectively, resulting in four reconstructed data sets $PBV_1$, $VNC_1$, $PBV_2$ and $VNC_2$ which include functional (perfusion) as well as anatomical information.

In a next step a transformation function T is determined which matches, when applied on the first VNC imaging data $VNC_1$, said first VNC imaging data with the second VNC imaging data $VNC_2$. Furthermore, this transformation function T can also be used to register said first PBV imaging data $PBV_1$ with the second PBV imaging data $PBV_2$, since they were reconstructed from the same CT imaging data sets $D_1$ and $D_2$ as the first and second reconstructed VNC imaging data $VNC_1$ and $VNC_2$. Additionally, when applying said transformation function T to the first PBV imaging data $PBV_1$ also a blood volume correction is performed which accounts for different blood volume content in the different respiratory phases. As a result, the four data sets $PBV_{1(registered)}$, $VNC_{1(registered)}$, $PBV_2$ and $VNC_2$ are now registered and provide quantitative anatomical as well as functional pulmonary information which can be directly compared on the regional level.

In a last step regional ventilation imaging data is calculated based on the registered first and second VNC imaging data $VNC_{1(registered)}$ and $VNC_2$. For this purpose the fractional air content in corresponding voxels of $VNC_{1(registered)}$ and $VNC_2$ are compared. Alternatively, the regional ventilation data can also be calculated from the determined transformation function T by the Jacobian determinant of T.

In the end the imaging processing method provides five registered imaging data sets (1 ventilation, 2 PBV from two respiratory phases, and 2 VNC from two respiratory phases), including three types of information (ventilation, perfusion, morphology), which can be regionally compared voxel by voxel. This enables a more precise evaluation of or correlation between the morphological and functional information of the respiratory system.

Figure 3:
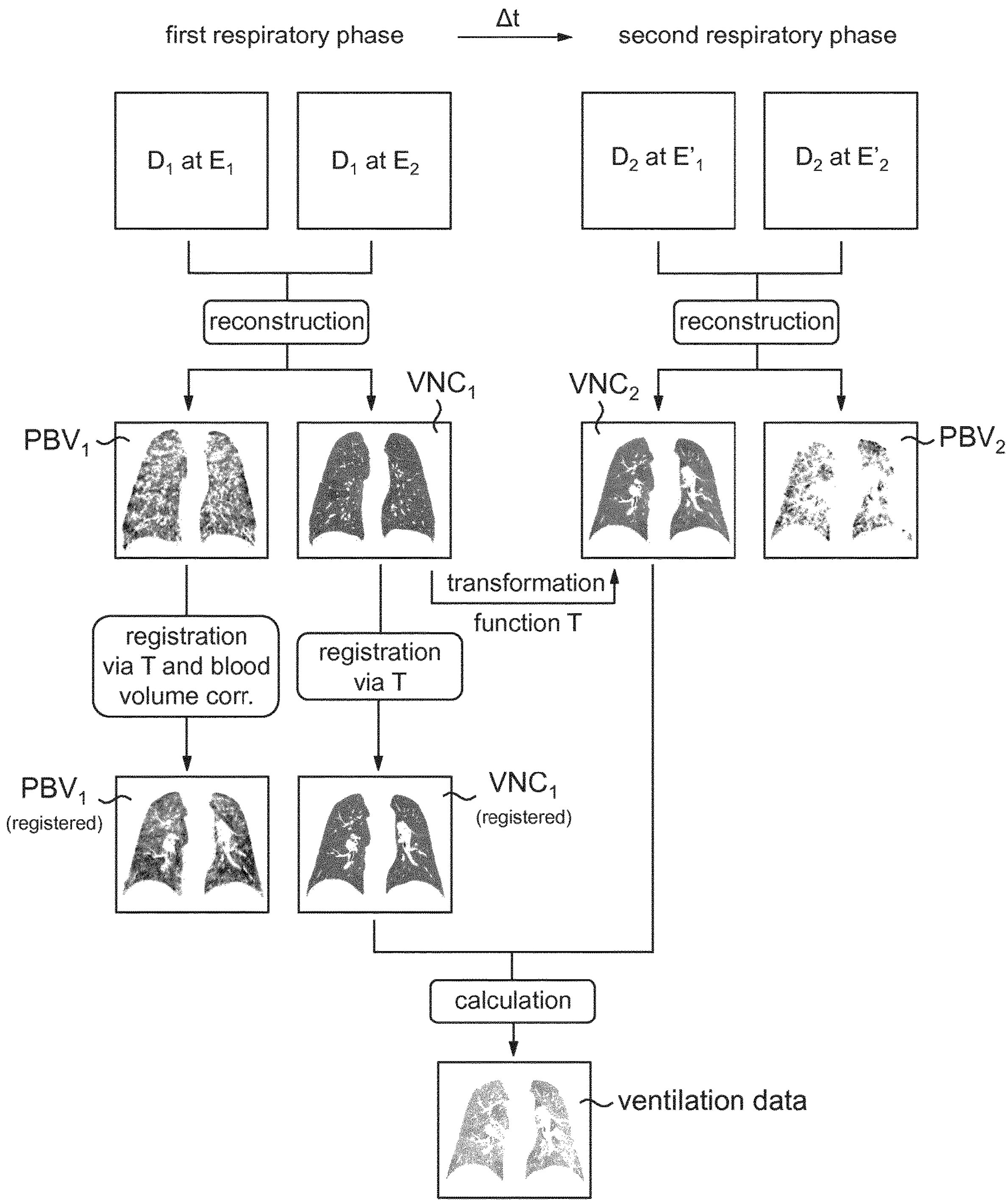
FIG. 3: Schematic illustration (processing pipeline) of the embodiment as shown in FIG. 2, including exemplary measured and processed morphological and functional CT imaging data of a human lung.

FIG. 3 shows the embodiment of the image processing method of FIG. 2 with exemplary measured and processed imaging data ($PBV_1$, $PBV_{1(registered)}$, $PBV_2$, $VNC_1$, $VNC_{1(registered)}$, $VNC_2$, and ventilation data). Since the sequence of imaging processing operations is identical to that of FIG. 2, in the following only the features and/or changes of the exemplary imaging data will be discussed. From the provided first and second (raw) CT imaging data $D_1$ and $D_2$ non-contrast coronal reformatted CT images of a human lung were reconstructed $VNC_1$ and $VNC_2$. Since $D_1$ and $D_2$ were obtained in two different respiratory phases of the subject consequently the shape of the lung differs in $VNC_1$ and $VNC_2$. Additionally, also the first and second regional reconstructed PBV imaging data $PBV_1$ and $PBV_2$ are shown. Thereby, the regional volume of blood to which fresh blood is being delivered is reflected in the regional contrast agent concentration (in the present case: iodine). Also in the PBV imaging data the different respiratory phases are notable in the different overall lung shape as well in the different regional iodine distribution. After the registration the local features of the PBV and VNC imaging data of the first respiratory phase $PBV_1$ and $VNC_1$ are transformed in order to match with the respective imaging data of the second respiratory phase $PBV_2$ and $VNC_2$. As can be seen in the images $PBV_{1(registered)}$ and $VNC_{1(registered)}$ the overall lung shape has changed compared to the not registered case before. Therefore, the morphological and functional information of the images of the first and second respiratory phase can be regionally compared voxel by voxel which enables a precise evaluation of the data in any following diagnostics. Finally, regional ventilation data were calculated based on the registered $VNC_{1(registered)}$ and $VNC_2$ imaging data. The ventilation data highlights regionally the rate at which new air reaches the gas exchange area of the lungs.

Figure 4:
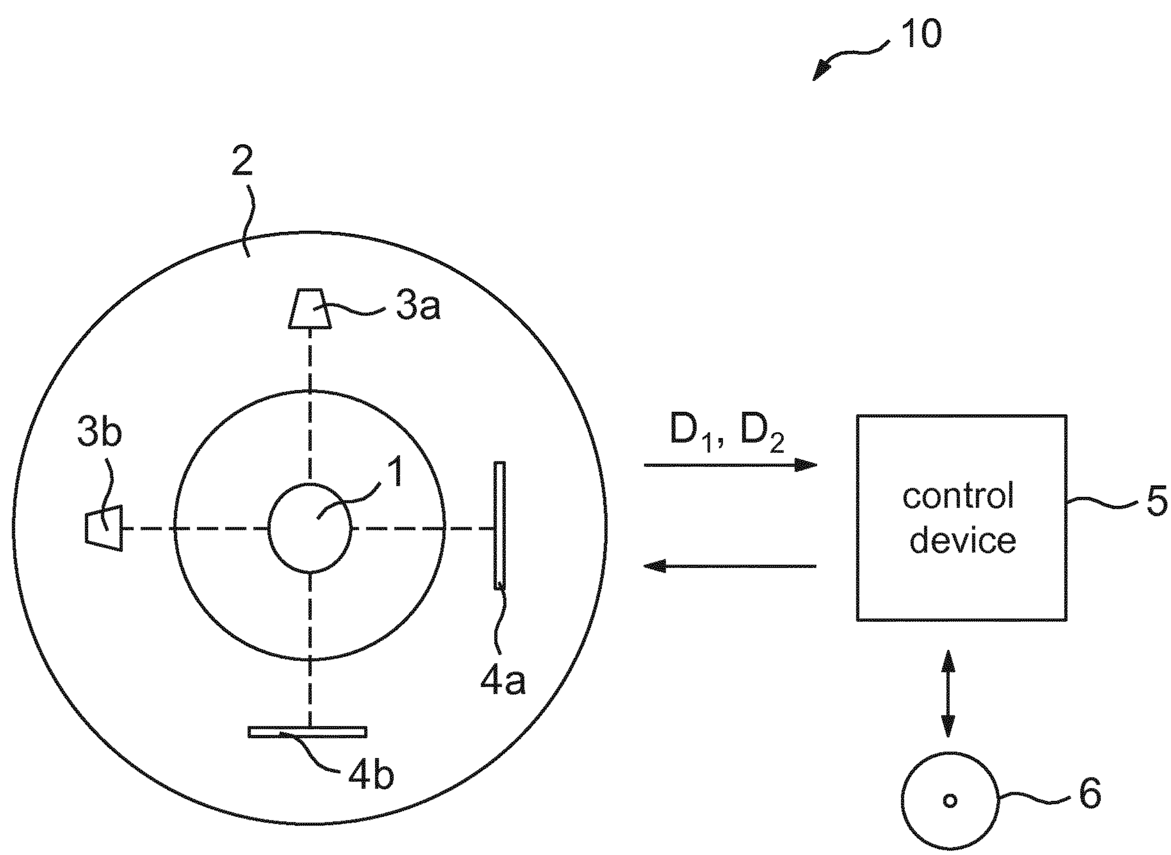
FIG. 4: Schematic illustration of a dual-source dual-energy CT scanning unit according to an embodiment of the invention.

FIG. 4 schematically shows an example of an dual-energy CT scanning unit 10 with a dual-source dual-energy CT scanner 2, including two separate x-ray tubes 3*a* and 3*b* and two corresponding detectors 4*a* and 4*b* which are placed orthogonally to each other within a single rotating gantry. Each tube can be operated at their own kilovoltage and miliampere settings, allowing for pairs of images of a subject 1 to be generated simultaneously, utilizing appropriate x-ray spectra for the separation of the material of interest (i.e. iodine). The pairs of CT images can be reconstructed from the multiple angles of view generated for each detector respectively. The dual-source dual-energy CT scanner 2 is connected to a control device 5, being adapted for controlling the dual-source dual-energy CT scanner 2, i.e. sending machine instructions to the scanner, and configured to perform a method according to the invention. The connection between the dual-source dual-energy CT scanner 2 and the control device 5 can be a wired, wireless, or any other type of data communication line which allows for a transfer of information between the dual-source dual-energy CT scanner 2 and the control device 5. Via the data communication line series of sets of raw imaging data $D_1$ and $D_2$ collected by the dual-source dual-energy CT scanner 2 are transferred to the control device 5 and subsequently processed with a method according to the invention. However, it is also possible that the imaging data $D_1$ and $D_2$ acquired by the dual-energy CT scanning unit 10 is transferred via a medium 6 or data network to another distant computer and processed there.

The features of the invention disclosed in the above description, the drawing and the claims can be of significance both individually as well as in combination or subcombination for the realisation of the invention in its various embodiments.

LIST OF REFERENCES

1] R. K. Kaza et al., Dual-Energy CT With Single- and Dual-Source Scanners: Current Applications in Evaluating the Genitourinary Tract, RadioGraphics, 32, 353, (2012)

[2] Chae et al., Xenon Ventilation CT with a Dual-Energy Technique of Dual-Source CT: Initial Experience, Radiol., 248, 615, (2008)

[3] Thieme et al., Pulmonary Ventilation and Perfusion Imaging With Dual-Energy CT, Eur. Radiol., 20, 2882, (2010)

[4] L. J. Zhang et al., Dual-Energy CT Lung Ventilation/Perfusion Imaging for Diagnosing Pulmonary Embolism, Eur. Radiol., 23, 2666, (2013)

[5] C. H. McCollough, Dual-Energy Algorithms and Post-processing Techniques, In: Dual Energy CT in Clinical Practice, Medical Radiology, Springer (2011)

[6] F. P. M. Oliveira and J. M. R. S. Tavares, Medical Image Registration: A Review, Comput. Methods. Biomech. Biomed. Eng., 17, 73 (2014)

[7] Guerrero et al., Dynamic Ventilation Imaging From Four-Dimensional Computed Tomography., Phys. Med. Biol., 51, 777 (2006)

[8] Castillo et al., Ventilation From Four-Dimensional Computed Tomography: Density Versus Jacobian Methods, Phys. Med. Biol., 55, 4661 (2010)

[9] K. Ding et al., Comparison of Image Registration Based Measures of Regional Lung Ventilation From Dynamic Spiral CT with Xe-CT, Med. Phys., 39, 5084 (2012)

[10] K. L. Grant et al., Assessment of an Advanced Image-Based Technique to Calculate Virtual Monoenergetic Computed Tomographic Images From a Dual-Energy Examination to Improve Contrast-to-Noise Ratio in Examinations Using Iodinated Contrast Media, Invest. Radiol., 49, 586, (2014)

[11] C. Schabel et al., Assessment of the Hepatic Veins in Poor Contrast Conditions Using Dual-Energy CT: Evaluation of a Novel Monoenergetic Extrapolation Software Algorithm, Rofo. 186, 591 (2014)

The invention claimed is:

1. A method for processing computed tomography (CT) imaging data (D) of a subject's respiratory system, wherein the subject has a CT-contrast enhancing agent distributed in its blood vessels, comprising:

providing first CT imaging data obtained at least at two x-ray energy levels ($E_1$, $E_2$) in a first respiratory phase of the subject;

providing second CT imaging data obtained at least at two x-ray energy levels ($E'_1$, $E'_2$) in a second respiratory phase, of the subject;

reconstructing first regional perfusion blood volume (PBV) imaging data from the provided first CT imaging data;

reconstructing second regional PBV imaging data from the provided second CT imaging data;

reconstructing first virtual non-contrast (VNC) imaging data from the provided first CT imaging data;

reconstructing second VNC imaging data from the provided second CT imaging data;

determining a transformation function T for registering the first and second reconstructed VNC imaging data;

registering the first and second reconstructed VNC imaging data by applying the transformation function T; and calculating regional ventilation imaging data using at least one of the registered first and second reconstructed VNC imaging data and the determined transformation function T.

2. Method according to claim 1, further comprising the step of:

registering the first and second reconstructed regional PBV imaging data by applying said transformation function T.

3. Method according to claim 1, further comprising the step of:

adjusting the first and/or second reconstructed regional PBV imaging data for different blood volume fractions caused by the different respiratory phases.

4. Method according to claim 1, further comprising at least one of:

a) reconstructing first morphological imaging data from the provided first CT imaging data; and b) reconstructing second morphological imaging data from the provided second CT imaging data.

5. Method according to claim 1, wherein the first CT imaging data obtained at least at the two x-ray energy levels ($E_1$, $E_2$) in an inhalation phase of the first respiratory phase of the subject is provided by acquiring the CT imaging data using a multi-energy CT scanner.

6. Method according to claim 5, wherein the second CT imaging data obtained at least at the two x-ray energy levels ($E'_1$, $E'_2$) in an exhalation phase of the second respiratory phase of the subject is provided by acquiring the CT imaging data using the multi-energy CT scanner.

7. Method according to claim 1, wherein in the step of determining the transformation function T, the first and second reconstructed VNC imaging data are used as reference data and floating data to determine the transformation function T which maps an image point in the reference data to the corresponding image point in the floating data.

8. Method according to claim 1, wherein the second CT imaging data of the second respiratory phase is obtained in a different respiratory phase, but in the same respiratory cycle with respect to the first respiratory phase.

9. Method according to claim 1, wherein the second CT imaging data of the second respiratory phase is obtained between 2 and 15 minutes after the first respiratory phase.

10. Method according to claim 1, wherein the first and second CT imaging data are obtained each at exactly the two x-ray energy levels ($E_1$ and $E_2$, $E'_1$ and $E'_2$) by using a dual-energy CT scanner.

11. Method according to claim 1, wherein the first and second CT imaging data are obtained each at more than the two x-ray energy levels ($E_1$, $E_2$, . . . , and $E_n$, $E'_1$, $E'_2$, . . . , and $E'_n$) by using a multi-energy CT scanner.

12. Method according to claim 1, wherein the two x-ray energy levels ($E_1$, $E_2$) of the first CT imaging data and the two x-ray energy levels ($E'_1$, $E'_2$) of the second CT imaging data are one of a) identical ($E_1=E'_1$, $E_2=E'_2$);

b) partly identical ($E_1=E'_1$, $E_2\neq E'_2$) and c) different ($E1\neq E'_1$, $E_2\neq E'_2$).

13. Method according to claim 1, further comprising the steps of:

providing third CT imaging data obtained at least at two x-ray energy levels ($E''_1$, $E''_2$) in a third respiratory phase of the subject;

reconstructing third regional PBV imaging data from the provided third CT imaging data of the third respiratory phase;

reconstructing third VNC imaging data from the provided third CT imaging data of the third respiratory phase;

determining a second transformation function $T_2$ for registering the third VNC imaging data with one of the first and second reconstructed VNC imaging data;

registering the third and one of the first and second reconstructed VNC imaging data by applying said second transformation function $T_2$, and calculating second regional ventilation imaging data using at least one of the registered third and the one of the first and second reconstructed VNC imaging data and the determined second transformation function $T_2$.

14. Method according to claim 13, wherein the spatial resolution of the first and second reconstructed regional PBV imaging data and the calculated regional ventilation imaging data is below 5 mm.

15. A non-transitory computer readable medium on which a computer program product is stored, the computer program product comprising a sequence of machine instructions that, when executed by a computer, causes the computer to execute the method according to claim 1.

16. A computer on which a computer program product is stored, the computer program product being processable by the computer, the computer program product comprising a sequence of machine instructions that, when executed by a computer, causes the computer to execute the method according to claim 1.

17. Computer according to claim 16, wherein the computer is formed as a control device for a CT scanning unit.

18. A Multi-energy CT scanning unit comprising a control device which is configured to perform a method according to claim 1.

19. A Multi-energy CT scanning unit comprising a control device which is configured to perform a method according the computer of claim 17.

* * * * *